US00PP26472P2

(12) United States Plant Patent
Shoaib et al.

(10) Patent No.: US PP26,472 P2
(45) Date of Patent: Mar. 8, 2016

(54) ***SCAEVOLA* PLANT NAMED 'BONSCA 1151'**

(50) Latin Name: *Scaevola aemula*
Varietal Denomination: BONSCA 1151

(71) Applicants: Mirza Mohammed Shoaib, Nort Parramata (AU); Andrew Bernuetz, Silverdale (AU)

(72) Inventors: Mirza Mohammed Shoaib, Nort Parramata (AU); Andrew Bernuetz, Silverdale (AU)

(73) Assignee: Bonza Botanicals PTY., LTD., Yellow Rock, NSW (AU)

( * ) Notice: Subject to any disclaimer, the term of this patent is extended or adjusted under 35 U.S.C. 154(b) by 181 days.

(21) Appl. No.: 13/999,237

(22) Filed: Jan. 31, 2014

(51) Int. Cl.
*A01H 5/02* (2006.01)

(52) U.S. Cl.
USPC ..... Plt./363

(58) Field of Classification Search
USPC ..... Plt./363
See application file for complete search history.

*Primary Examiner* — Anne Grunberg
(74) *Attorney, Agent, or Firm* — C. A. Whealy

(57) ABSTRACT

A new and distinct cultivar of *Scaevola* plant named 'BONSCA 1151', characterized by its mounded and semi-trailing plant habit; vigorous growth habit; freely branching habit; variegated leaves; freely flowering habit; long flowering period; bright purple-colored flowers; and good container and garden performance.

1 Drawing Sheet

Botanical designation: *Scaevola aemula.*
Cultivar denomination: 'BONSCA 1151'.

BACKGROUND OF THE INVENTION

The present invention relates to a new and distinct cultivar of *Scaevola* plant, botanically known as *Scaevola aemula* and hereinafter referred to by the name 'BONSCA 1151'.

The new *Scaevola* plant a product of a planned breeding program conducted by the Inventors in Yellow Rock, New South Wales, Australia. The objective of the breeding program is to create new mounding, semi-trailing and freely-flowering *Scaevola* plants with variegated leaves and attractive flower color.

The new *Scaevola* plant originated from an open-pollination in Yellow Rock, New South Wales, Australia in November, 2009 of an unnamed proprietary selection of *Scaevola aemula*, not patented, as the female, or seed, parent with an unknown proprietary selection of *Scaevola aemula,* as the male, or pollen, parent. The new *Scaevola* plant was discovered and selected by the Inventors as a single flowering plant from within the progeny of the stated open-pollination in a controlled greenhouse environment in Yellow Rock, New South Wales, Australia on Mar. 15, 2011.

Asexual reproduction of the new *Scaevola* plant by vegetative cuttings in a controlled environment in Yellow Rock, New South Wales, Australia since Mar. 15, 2011 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BONSCA 1151'. These characteristics in combination distinguish 'BONSCA 1151' as a new and distinct *Scaevola* plant:

1. Mounded and semi-trailing plant habit.
2. Vigorous growth habit.
3. Freely branching habit.
4. Variegated leaves.
5. Freely flowering habit.
6. Long flowering period.
7. Bright purple-colored flowers.
8. Good container and garden performance.

Plants of the new *Scaevola* can be compared to plants of the female parent selection. Plants of the new *Scaevola* differ from plants of the female parent selection primarily in leaf and flower color.

Plants of the new *Scaevola* can be compared to plants of the *Scaevola aemula* 'Bonscalib', disclosed in U.S. Plant Pat. No. 19,516. In side-by-side comparisons, plants of the new *Scaevola* differed from plants of the 'Bonscalib' in the following characteristics:

1. Plants of the new *Scaevola* were larger than plants of 'Bonscalib'.
2. Plants of the new *Scaevola* had variegated leaves whereas plants of 'Bonscalib' did not have variegated leaves.
3. Plants of the new *Scaevola* had smaller flowers than plants of 'Bonscalib'.
4. Flowers of plants of the new *Scaevola* and 'Bonscalib' differed in flower color.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph at the top of the sheet comprises a side perspective view of a typical flowering plant of 'BONSCA 1151' grown in a container.

The photograph at the bottom of the sheet is a close-up view of a typical flowering plant of 'BONSCA 1151'.

DETAILED BOTANICAL DESCRIPTION

The aforementioned photographs and following observations, measurements and values describe plants grown in 20-cm containers during the summer in an outdoor nursery in Higashiomi, Shiga, Japan and under cultural practices typical of commercial *Scaevola* production. During the production of the plants, day temperatures ranged from 15° C. to 30° C. and night temperatures ranged from 13° C. to 25° C. Plants were four months old when the photographs were taken and five months old when the detailed description was taken. In the following description, color references are made to The Royal Horticultural Society Colour Chart, 2001 Edition, except where general terms of ordinary dictionary significance are used.

Botanical classification: *Scaevola aemula* 'BONSCA 1151'.

Parentage:

*Female, or seed, parent*.—Unnamed proprietary selection of *Scaevola aemula,* not patented.

*Male or pollen parent*.—Unknown proprietary selection of *Scaevola aemula,* not patented.

Propagation:

*Type*.—By vegetative cuttings.

*Time to initiate roots, summer*.—About ten days at temperatures about 21° C. to 25° C.

*Time to initiate roots, winter*.—About 15 days at temperatures about 18° C. to 21° C.

*Time to develop roots, summer*.—About three weeks at temperatures about 21° C. to 25° C.

*Time to develop roots, winter*.—About four weeks at temperatures about 18° C. to 21° C.

*Root description*.—Fibrous; white in color.

*Rooting habit*.—Freely branching; moderately dense.

Plant description:

*Plant form and growth habit*.—Mounded and semi-trailing plant habit; medium in plant size; vigorous growth habit.

*Branching habit*.—Freely branching habit with lateral branches potentially forming at every node; pinching enhances branching potential.

*Plant height*.—About 16.8 cm.

*Plant diameter* (*area of spread*).—About 62 cm.

Lateral branch description:

*Length*.—About 36.3 cm.

*Diameter*.—About 2.9 mm.

*Internode length*.—About 2.5 cm.

*Aspect*.—Outwardly, decumbent.

*Texture*.—Pubescent.

*Color*.—Close to 138A overlain with close to N77A.

Leaf description:

*Arrangement*.—Alternate, simple; sessile.

*Length*.—About 4 cm.

*Width*.—About 1.9 cm.

*Shape*.—Narrowly spatulate.

*Apex*.—Acute.

*Base*.—Cuneate.

*Margin*.—Serrate.

*Texture, upper and lower surfaces*.—Pubescent; slightly coarse.

*Venation pattern*.—Pinnate, reticulate.

*Color*.—Developing leaves, upper surface: Close to 137B, towards the margins, close to 145C. Developing leaves, lower surface: Close to 138B; towards the margins, close to 145D. Fully expanded leaves, upper surface: Close to 138A, towards the margins, close to 150C; random sectors, close to 145B, 145C and 150C; venation, close to 137C. Fully expanded leaves, lower surface: Close to 147C; towards the margins, close to 150C; venation, close to 138B.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from leaf axils; flowers face upright to outwardly; freely flowering habit with typically about 198 flowers developing per plant.

*Flowering time*.—Plants begin flowering after about four weeks after planting; long flower period, plants flower continuously from spring to late autumn in Japan.

*Flower longevity*.—Flowers typically last about a week on the plant; flowers persistent.

*Fragrance*.—None detected.

*Flower buds*.—Length: About 1.9 cm. Diameter: About 3.6 mm. Shape: Lenticular. Color: Close to 76A.

*Flowers*.—Diameter: About 1.4 cm by 2.6 cm. Tube length: About 1.1 cm. Tube diameter: About 2.9 mm.

*Petals*.—Quantity per flower: Five, fused at base. Length, above tube: About 1.1 cm. Width, above tube: About 3.4 mm. Shape: Narrowly elliptic. Apex: Mucronate. Margin: Entire. Texture, upper and lower surfaces: Smooth, glabrous. Color: When opening, upper surface: Close to N82A. When opening, lower surface: Close to N82B; longitudinal central stripe, close to 155C and 145B. Fully opened, upper surface: Close to N82B; towards the base, close to 4C; venation, close to 187A. Fully opened, lower surface: Close to N82C; longitudinal central stripe, close to 155C and 145B. Throat: Close to 1B; venation, close to 79A. Tube: Close to 4C; venation, close to 79C.

*Sepals*.—Quantity per flower: Two. Length: About 8.3 mm. Width: About 1.7 mm. Shape: Lanceolate. Apex: Acute. Base: Decurrent. Margin: Entire. Texture, upper and lower surfaces: Slightly pubescent. Color: When developing, upper surface: Close to 138A; towards the margins, close to 142C. When developing, lower surface: Close to 138A; towards the margins, close to 142D. Fully opened, upper and lower surfaces: Close to 138A; towards the margins, close to 144D.

*Reproductive organs*.—Androecium: Stamen quantity per flower: Five. Anther shape: Ellipsoidal. Anther size: About 1.9 mm by 0.4 mm. Anther color: Close to 166A. Pollen: Scarce. Gynoecium: Pistil quantity per flower: One. Pistil length: About 9.3 mm. Style color: Close to 72B and 157A. Stigma shape: Narrowly oblong. Stigma color: Close to 145C. Ovary color: Close to 144D.

*Seeds and fruits*.—Seed and fruit development have not been observed on plants of the new *Scaevola*.

Garden performance: Plants of the new *Scaevola* have been observed to have good garden performance and to tolerate rain, wind and temperatures ranging from about 0° C. to about 40° C.

Pathogen & pest resistance: Plants of the new *Scaevola* have not been shown to be resistant to pathogens and pests common to *Scaevola* plants.

It is claimed:

1. A new and distinct *Scaevola* plant named 'BONSCA 1151' as illustrated and described.

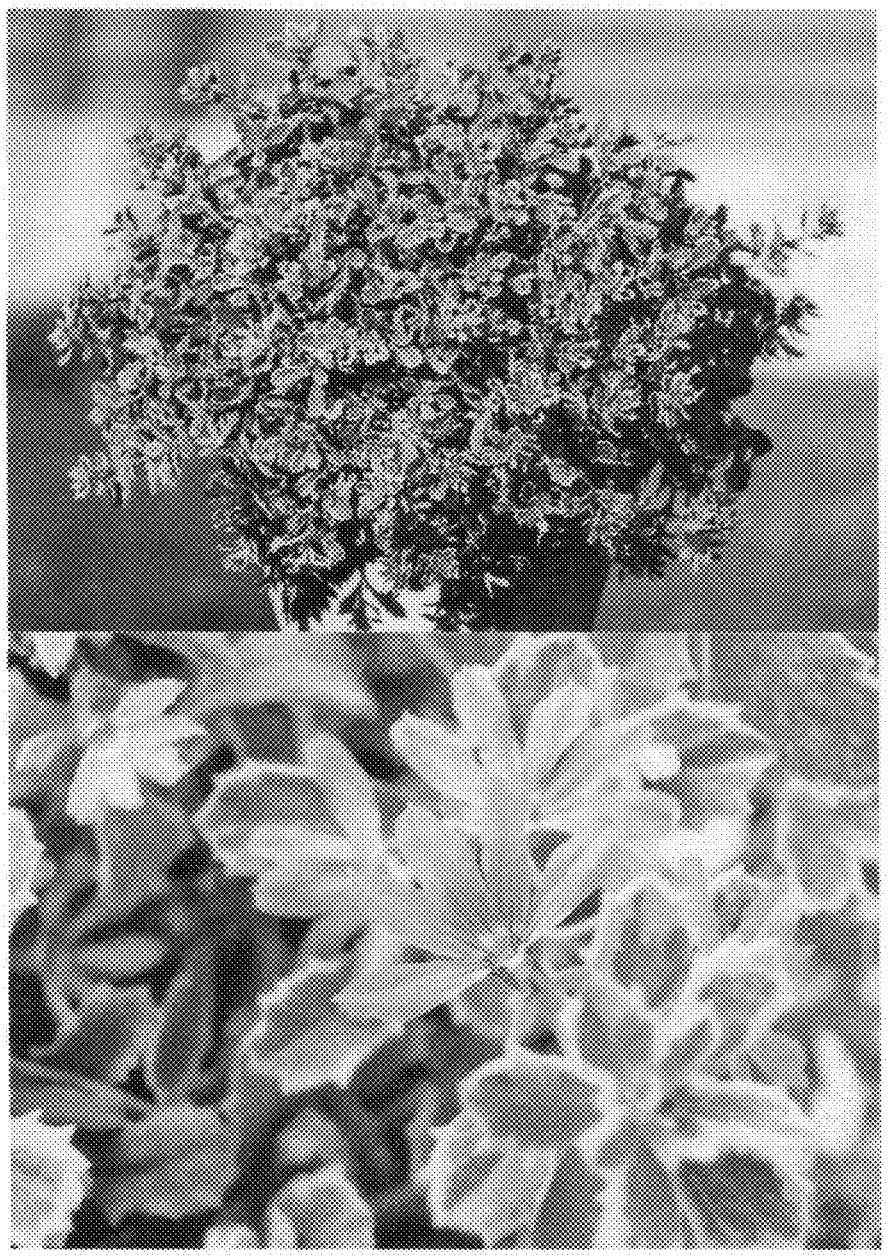

* * * * *